US008936601B2

(12) United States Patent
Carignan et al.

(10) Patent No.: US 8,936,601 B2
(45) Date of Patent: *Jan. 20, 2015

(54) MARKING TEMPLATE FOR INSTALLING A CUSTOM REPLACEMENT DEVICE FOR RESURFACING A FEMUR AND ASSOCIATED INSTALLATION METHOD

(71) Applicant: Kinamed, Inc., Camarillo, CA (US)

(72) Inventors: Roger Carignan, Williams, AZ (US); Clyde R. Pratt, Somis, CA (US)

(73) Assignee: Kinamed, Inc., Camarillo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/206,494

(22) Filed: Mar. 12, 2014

(65) Prior Publication Data

US 2014/0194997 A1 Jul. 10, 2014

Related U.S. Application Data

(60) Continuation of application No. 13/096,868, filed on Apr. 28, 2011, now Pat. No. 8,771,281, which is a continuation of application No. 12/120,581, filed on May 14, 2008, now Pat. No. 7,935,150, which is a
(Continued)

(51) Int. Cl.
*A61B 17/58* (2006.01)
*A61F 2/00* (2006.01)
(Continued)

(52) U.S. Cl.
CPC ............ *A61F 2/3859* (2013.01); *A61B 17/1764* (2013.01); *A61F 2/30942* (2013.01);
(Continued)

(58) Field of Classification Search
USPC ............ 623/20.35, 20.3–20.32, 20.18, 20.14, 623/20.15, 20.11, 18.11, 16.11, 20.19, 623/20.21; 606/80, 96, 53, 85–88, 99, 101
See application file for complete search history.

(56) References Cited

U.S. PATENT DOCUMENTS 3,748,662 A 7/1973 Helfet
3,748,682 A * 7/1973 Rhodes .................. 15/229.1
(Continued)

FOREIGN PATENT DOCUMENTS

BE 1011205 6/1999
DE 33 05 237 2/1983
(Continued)

OTHER PUBLICATIONS

Anderson, "Role of Rapid Prototyping in Preoperative Planning and Patient-Specific Implant Generation," *Biomedical Engineering Conference, Proceedings of the 1996 Fifteenth Southern*: 558-559 (1996).
(Continued)

*Primary Examiner* — Alvin Stewart
(74) *Attorney, Agent, or Firm* — Koppel, Patrick, Heybl & Philpott

(57) ABSTRACT

A replacement device for resurfacing a joint surface of a femur and a method of making and installing such a device is provided. The custom replacement device is designed to substantially fit the trochlear groove surface, of an individual femur, thereby creating a "customized" replacement device for that individual femur and maintaining the original kinematics of the joint. The top surface is designed so as to maintain centrally directed tracking of the patella perpendicular to the plane established by the distal end of the femoral condyles and aligned with the center of the femoral head.

28 Claims, 6 Drawing Sheets

Related U.S. Application Data continuation of application No. 11/030,868, filed on Jan. 7, 2005, now Pat. No. 7,517,365, which is a division of application No. 10/712,436, filed on Nov. 12, 2003, now Pat. No. 6,905,514, which is a division of application No. 09/528,128, filed on Mar. 17, 2000, now Pat. No. 6,712,856.

(51) Int. Cl.
| | |
|---|---|
| A61F 2/38 | (2006.01) |
| A61B 17/17 | (2006.01) |
| A61F 2/30 | (2006.01) |
| A61F 2/46 | (2006.01) |
| A61B 17/00 | (2006.01) |

(52) U.S. Cl.
CPC ............... *A61F2/3877* (2013.01); *A61F 2/461* (2013.01); *A61B 17/00491* (2013.01); *A61F 2/30767* (2013.01); *A61F 2002/30125* (2013.01); *A61F 2002/30594* (2013.01); *A61F 2002/30685* (2013.01); *A61F 2002/30892* (2013.01); *A61F 2002/30948* (2013.01); *A61F 2002/30952* (2013.01); *A61F 2002/30957* (2013.01); *A61F 2230/0008* (2013.01); *A61F 2310/00017* (2013.01); *A61F 2310/00023* (2013.01); *A61F 2310/00029* (2013.01); *A61F 2310/00203* (2013.01); *A61F 2310/00239* (2013.01); *A61F 2310/00407* (2013.01); *A61F 2310/00796* (2013.01); *Y10S 623/901* (2013.01)
USPC ............................................. 606/96; 623/901

(56) References Cited

U.S. PATENT DOCUMENTS

| | | | | |
|---|---|---|---|---|
| 3,798,679 A | * | 3/1974 | Ewald | 623/20.31 |
| 3,878,566 A | * | 4/1975 | Bechtol | 623/20.19 |
| 4,007,495 A | * | 2/1977 | Frazier | 623/20.19 |
| 4,008,720 A | * | 2/1977 | Brinckmann et al. | 606/53 |
| 4,011,451 A | * | 3/1977 | Nelson | 250/343 |
| 4,052,753 A | * | 10/1977 | Dedo | 623/14.12 |
| 4,151,615 A | * | 5/1979 | Hall | 623/20.19 |
| 4,178,641 A | * | 12/1979 | Grundei et al. | 623/20.31 |
| 4,213,209 A | * | 7/1980 | Insall et al. | 623/20.27 |
| 4,246,895 A | * | 1/1981 | Rehder | 606/89 |
| 4,427,005 A | * | 1/1984 | Tener | 606/186 |
| 4,436,684 A | * | 3/1984 | White | 264/138 |
| 4,467,801 A | * | 8/1984 | Whiteside | 606/88 |
| 4,502,161 A | * | 3/1985 | Wall | 623/14.12 |
| 4,575,330 A | * | 3/1986 | Hull | 425/174.4 |
| 4,575,805 A | * | 3/1986 | Moermann et al. | 700/163 |
| 4,611,288 A | * | 9/1986 | Duret et al. | 700/163 |
| 4,646,729 A | * | 3/1987 | Kenna et al. | 606/88 |
| 4,663,720 A | * | 5/1987 | Duret et al. | 700/163 |
| 4,692,140 A | * | 9/1987 | Olson | 604/40 |
| 4,703,751 A | * | 11/1987 | Pohl | 606/62 |
| 4,704,686 A | * | 11/1987 | Aldinger | 700/163 |
| 4,742,464 A | * | 5/1988 | Duret et al. | 700/183 |
| 4,748,511 A | * | 5/1988 | Nichols et al. | 382/232 |
| 4,759,350 A | * | 7/1988 | Dunn et al. | 606/82 |
| 4,791,934 A | * | 12/1988 | Brunnett | 600/429 |
| 4,822,365 A | * | 4/1989 | Walker et al. | 128/898 |
| 4,841,975 A | * | 6/1989 | Woolson | 600/425 |
| 4,888,021 A | * | 12/1989 | Forte et al. | 623/20.19 |
| 4,903,202 A | * | 2/1990 | Crawford | 382/131 |
| 4,905,148 A | * | 2/1990 | Crawford | 382/131 |
| 4,922,915 A | | 5/1990 | Arnold et al. | |
| 4,923,459 A | * | 5/1990 | Nambu | 606/130 |
| 4,936,862 A | * | 6/1990 | Walker et al. | 128/898 |
| 4,940,412 A | * | 7/1990 | Blumenthal | 434/267 |
| 4,976,737 A | * | 12/1990 | Leake | 128/898 |
| 5,007,936 A | * | 4/1991 | Woolson | 128/898 |
| 5,011,469 A | * | 4/1991 | Buckberg et al. | 604/6.11 |
| 5,015,424 A | * | 5/1991 | Smalley | 264/401 |
| 5,021,061 A | * | 6/1991 | Wevers et al. | 623/20.18 |
| 5,030,219 A | * | 7/1991 | Matsen et al. | 606/53 |
| 5,071,337 A | * | 12/1991 | Heller et al. | 425/174.4 |
| 5,098,383 A | * | 3/1992 | Hemmy et al. | 604/116 |
| 5,098,437 A | * | 3/1992 | Kashuba et al. | 606/89 |
| 5,100,408 A | * | 3/1992 | Lackey | 606/79 |
| 5,122,142 A | * | 6/1992 | Pascaloff | 606/82 |
| 5,123,927 A | * | 6/1992 | Duncan et al. | 623/20.21 |
| 5,129,908 A | * | 7/1992 | Petersen | 606/88 |
| 5,141,680 A | * | 8/1992 | Almquist et al. | 264/401 |
| 5,150,304 A | * | 9/1992 | Berchem et al. | 700/182 |
| 5,151,813 A | * | 9/1992 | Yamamoto et al. | 359/202.1 |
| 5,156,777 A | * | 10/1992 | Kaye | 264/40.1 |
| 5,192,559 A | * | 3/1993 | Hull et al. | 425/89 |
| 5,198,159 A | * | 3/1993 | Nakamura et al. | 264/401 |
| 5,226,915 A | * | 7/1993 | Bertin | 623/20.15 |
| 5,235,510 A | * | 8/1993 | Yamada et al. | 600/300 |
| 5,238,497 A | * | 8/1993 | Segawa | 118/641 |
| 5,260,985 A | * | 11/1993 | Mosby | 378/164 |
| 5,273,429 A | * | 12/1993 | Rekow et al. | 433/215 |
| 5,274,565 A | * | 12/1993 | Reuben | 700/182 |
| 5,282,803 A | * | 2/1994 | Lackey | 606/80 |
| 5,291,401 A | * | 3/1994 | Robinson | 382/132 |
| 5,301,117 A | * | 4/1994 | Riga | 700/118 |
| 5,312,408 A | * | 5/1994 | Brown | 606/80 |
| 5,320,529 A | * | 6/1994 | Pompa | 433/76 |
| 5,320,625 A | * | 6/1994 | Bertin | 606/91 |
| 5,330,477 A | * | 7/1994 | Crook | 606/33 |
| 5,344,458 A | * | 9/1994 | Bonutti | 623/20.32 |
| 5,360,446 A | * | 11/1994 | Kennedy | 128/898 |
| 5,362,427 A | * | 11/1994 | Mitchell, Jr. | 264/497 |
| 5,365,996 A | * | 11/1994 | Crook | 164/45 |
| 5,370,692 A | * | 12/1994 | Fink et al. | 128/898 |
| 5,376,126 A | * | 12/1994 | Lin | 623/23.11 |
| 5,415,820 A | * | 5/1995 | Furuta et al. | 264/401 |
| 5,417,694 A | * | 5/1995 | Marik et al. | 606/88 |
| 5,432,045 A | * | 7/1995 | Narukawa et al. | 430/269 |
| 5,448,489 A | * | 9/1995 | Reuben | 700/163 |
| 5,452,219 A | * | 9/1995 | Dehoff et al. | 700/163 |
| 5,452,407 A | * | 9/1995 | Crook | 345/421 |
| 5,458,645 A | * | 10/1995 | Bertin | 128/898 |
| 5,474,560 A | * | 12/1995 | Rohr, Jr. | 606/91 |
| 5,486,181 A | * | 1/1996 | Cohen et al. | 606/91 |
| 5,503,149 A | * | 4/1996 | Beavin | 600/411 |
| 5,512,920 A | * | 4/1996 | Gibson | 345/163 |
| 5,514,140 A | * | 5/1996 | Lackey | 606/80 |
| 5,514,519 A | * | 5/1996 | Neckers | 430/269 |
| 5,534,104 A | * | 7/1996 | Langer et al. | 156/275.5 |
| 5,545,995 A | * | 8/1996 | Schneider et al. | 324/318 |
| 5,554,190 A | * | 9/1996 | Draenert | 128/898 |
| 5,555,884 A | * | 9/1996 | Nonomura | 600/420 |
| 5,569,251 A | * | 10/1996 | Baker et al. | 606/281 |
| 5,593,450 A | * | 1/1997 | Scott et al. | 623/20.18 |
| 5,595,703 A | * | 1/1997 | Swaelens et al. | 264/401 |
| 5,609,640 A | * | 3/1997 | Johnson | 623/20.2 |
| 5,626,919 A | * | 5/1997 | Chapman et al. | 427/510 |
| 5,628,749 A | * | 5/1997 | Vendrely et al. | 606/80 |
| 5,634,927 A | * | 6/1997 | Houston et al. | 606/96 |
| 5,682,886 A | * | 11/1997 | Delp et al. | 600/407 |
| 5,682,890 A | * | 11/1997 | Kormos et al. | 600/417 |
| 5,683,243 A | * | 11/1997 | Andreiko et al. | 433/3 |
| 5,702,459 A | * | 12/1997 | Hummer et al. | 623/20.18 |
| 5,709,689 A | * | 1/1998 | Ferrante et al. | 606/86 R |
| 5,715,836 A | * | 2/1998 | Kliegis et al. | 600/425 |
| 5,718,585 A | * | 2/1998 | Dehoff et al. | 433/202.1 |
| 5,728,162 A | * | 3/1998 | Eckhoff | 623/20.31 |
| 5,735,277 A | * | 4/1998 | Schuster | 600/425 |
| 5,741,215 A | * | 4/1998 | D'Urso | 600/407 |
| 5,755,803 A | * | 5/1998 | Haines et al. | 623/20.14 |
| 5,762,125 A | * | 6/1998 | Mastrorio | 164/4.1 |
| 5,765,561 A | * | 6/1998 | Chen et al. | 600/407 |
| 5,768,134 A | * | 6/1998 | Swaelens et al. | 700/121 |
| 5,769,092 A | * | 6/1998 | Williamson, Jr. | 128/898 |
| 5,769,855 A | * | 6/1998 | Bertin et al. | 606/88 |
| 5,769,856 A | * | 6/1998 | Dong et al. | 606/96 |
| 5,798,924 A | * | 8/1998 | Eufinger et al. | 700/117 |
| 5,824,085 A | * | 10/1998 | Sahay et al. | 128/898 |
| 5,824,098 A | * | 10/1998 | Stein | 623/20.18 |

(56) References Cited

U.S. PATENT DOCUMENTS

| | | | | |
|---|---|---|---|---|
| 5,832,415 | A * | 11/1998 | Wilkening et al. | 702/86 |
| 5,851,207 | A * | 12/1998 | Cesarone | 606/86 B |
| 5,857,853 | A * | 1/1999 | van Nifterick et al. | 433/213 |
| 5,860,981 | A * | 1/1999 | Bertin et al. | 606/89 |
| 5,871,018 | A * | 2/1999 | Delp et al. | 128/898 |
| 5,880,976 | A * | 3/1999 | DiGioia, III et al. | 703/7 |
| 5,904,890 | A * | 5/1999 | Lohner et al. | 264/401 |
| 5,925,049 | A * | 7/1999 | Gustilo et al. | 606/82 |
| 5,945,994 | A * | 8/1999 | Shimizu et al. | 345/418 |
| 5,976,148 | A * | 11/1999 | Charpenet et al. | 606/91 |
| 5,995,738 | A * | 11/1999 | DiGioia et al. | 703/11 |
| 6,002,859 | A * | 12/1999 | DiGioia et al. | 703/11 |
| 6,007,537 | A * | 12/1999 | Burkinshaw et al. | 606/66 |
| 6,013,079 | A * | 1/2000 | Salam | 606/82 |
| 6,171,340 | B1 * | 1/2001 | McDowell | 623/18.11 |
| 6,190,415 | B1 * | 2/2001 | Cooke et al. | 623/20.33 |
| 6,197,064 | B1 * | 3/2001 | Haines et al. | 623/20.31 |
| 6,231,611 | B1 * | 5/2001 | Mosseri | 623/22.12 |
| 6,235,060 | B1 * | 5/2001 | Kubein-Meesenburg et al. | 623/20.31 |
| 6,327,491 | B1 * | 12/2001 | Franklin et al. | 600/429 |
| 6,379,386 | B1 * | 4/2002 | Resch et al. | 623/19.13 |
| 6,463,351 | B1 * | 10/2002 | Clynch | 700/163 |
| 6,616,696 | B1 * | 9/2003 | Merchant | 623/20.18 |
| 6,712,856 | B1 * | 3/2004 | Carignan et al. | 623/20.35 |
| 6,772,026 | B2 * | 8/2004 | Bradbury et al. | 700/98 |
| 6,905,514 | B2 * | 6/2005 | Carignan et al. | 623/20.35 |
| 7,121,832 | B2 * | 10/2006 | Hsieh et al. | 434/262 |
| 7,258,701 | B2 * | 8/2007 | Aram et al. | 623/20.15 |
| 7,468,075 | B2 * | 12/2008 | Lang et al. | 623/16.11 |
| 7,517,365 | B2 * | 4/2009 | Carignan et al. | 623/20.35 |
| 7,534,263 | B2 * | 5/2009 | Burdulis et al. | 623/14.12 |
| 7,544,209 | B2 * | 6/2009 | Lotke | 623/20.19 |
| 7,618,451 | B2 * | 11/2009 | Berez et al. | 623/14.12 |
| 7,634,119 | B2 * | 12/2009 | Tsougarakis et al. | 382/128 |
| 7,636,459 | B2 * | 12/2009 | Dore et al. | 382/128 |
| 7,651,506 | B2 * | 1/2010 | Bova et al. | 606/130 |
| 7,686,989 | B2 * | 3/2010 | Van der Zel | 264/20 |
| 7,758,799 | B2 * | 7/2010 | Hull et al. | 264/401 |
| D622,854 | S * | 8/2010 | Otto et al. | D24/155 |
| 7,806,896 | B1 * | 10/2010 | Bonutti | 606/86 R |
| 7,935,150 | B2 * | 5/2011 | Carignan et al. | 623/20.35 |
| 7,981,158 | B2 * | 7/2011 | Fitz et al. | 623/17.16 |
| 8,419,741 | B2 * | 4/2013 | Carignan et al. | 606/88 |
| 8,771,281 | B2 * | 7/2014 | Carignan et al. | 606/88 |
| 2002/0198528 | A1 * | 12/2002 | Engh et al. | 606/79 |
| 2004/0098133 | A1 * | 5/2004 | Carignan et al. | 623/20.35 |
| 2005/0119664 | A1 * | 6/2005 | Carignan et al. | 606/96 |
| 2006/0058884 | A1 * | 3/2006 | Aram et al. | 623/20.15 |
| 2008/0215059 | A1 * | 9/2008 | Carignan et al. | 606/96 |
| 2011/0276145 | A1 * | 11/2011 | Carignan et al. | 623/20.35 |
| 2012/0158002 | A1 * | 6/2012 | Carignan et al. | 606/89 |
| 2012/0165821 | A1 * | 6/2012 | Carignan et al. | 606/89 |
| 2013/0184764 | A1 * | 7/2013 | Stone et al. | 606/280 |
| 2014/0189993 | A1 * | 7/2014 | Carignan et al. | 29/407.01 |
| 2014/0194998 | A1 * | 7/2014 | Carignan et al. | 623/20.35 |

FOREIGN PATENT DOCUMENTS

| | | |
|---|---|---|
| DE | 3522196 | 2/1986 |
| DE | 3626549 | 2/1988 |
| DE | 4125534 | 2/1993 |
| DE | 4304572 A1 | 8/1994 |
| DE | 4328490 | 3/1995 |
| DE | 4417083 | 11/1995 |
| EP | 0 336 861 | 10/1989 |
| EP | 0338751 | 10/1989 |
| EP | 0348061 | 12/1989 |
| EP | 0416124 | 3/1991 |
| EP | 0484183 | 5/1992 |
| EP | 0498685 | 8/1992 |
| EP | 0 685 210 | 12/1995 |
| EP | 0610146 | 7/1998 |
| EP | 0908836 A2 | 4/1999 |
| FR | 2 682 589 | 4/1993 |
| FR | 2684590 | 6/1993 |
| FR | 2704746 | 10/1994 |
| GB | 1061230 | 3/1967 |
| GB | 2085757 | 5/1982 |
| GB | 2 215 610 | 9/1989 |
| JP | 2052725 | 2/1990 |
| WO | WO92/18323 | 10/1992 |
| WO | WO92/20505 | 11/1992 |
| WO | WO92/22265 | 12/1992 |
| WO | WO93/25157 | 12/1993 |
| WO | WO 94/13214 | 6/1994 |
| WO | WO97/29901 | 8/1997 |

OTHER PUBLICATIONS

Ateshian, et al., "Quantitative Anatomy of Diarthrodial Joint Articular Layers," Basic Orthopaedic Biomechanics, 2d. Ed: 253-273 (1997).

Birnbaum, et al., "Computer-Assisted Orthopedic Surgery with Individual Templates and Comparison to Conventional Operation Method," Spine, 26, (4):365-370 (2001).

Bono "Digital Templating in Total Hip Arthroplasty," The Journal of Bone & Joint Surgery, 86-A (supp).2):118-122 (2004).

Cohen, et al, "Computer-Aided Planning of Patellofemoral Joint OA Surgery: Developing Physical Models from Patient MRI" Medical Image Computing and Computer-Assisted Interventation—MICCAI'98 Lecture Notes in Computer Science, 1496, 9-20, DOI: 10.1007/BFb0056183 (1998).

Cohen, et al, "Knee cartilage topography, thickness, and contact areas from MRI: in-vitro calibration and in-vivo measurements," Osteoarthritis and Cartilage,7(1):95-109 (1999).

Kwak, et al., "An Anatomically Based 3-D Coordinate System for the Knee Joint," 1995 Advances in Bioengineering, BED-31:309-310 (1995).

Kshirsagar, et al., "Measurement of Localized Cartilage Volume and Thickness of Human Knee Joints by Computer Analysis of Three-Dimensional Magnetic Resonance Images," Investigative Radiology, 33(5):289-299 (1998).

Peterfy, "MRI in the Assessment of Synovium and Cartilage," British Journal of Rheumatology, 35(suppl.3):3-5 (1996).

Radermacher, et al., "CT Image-Based Planning and Execution of Interventions in Orthopedic Surgery Using Individual Templates—Experimental Results and Aspects of Clinical Applications" In Nolte, LP, Ganz R (eds). CAOS—Computer Assisted Orthopaedic Surgery Bern, Hans Huber 42-52 (1998).

Radermacher, et al., "Computer Assisted Orthopedic Surgery with Image Based Individual Templates," Clinical Orthopaedics and Related Research, 354:28-38 (1998).

Radermacher, "Computerunterstützte Operationsplanung und—ausführung mittels individueller Bearbeitungsschablonen in der Orthopädie" Helmholtz-Institut für Biomedizinische Technik an der RWTH Aachen, Shaker Vortag D 82: 1-234 (1999).

Recht, et al., "MR Imaging of Articular Cartilage: Current Status and Future Directions," AJR, 163:283-290(1994).

Staudte, "Computergestützte Operations-planung und—tehnik in der Orthopädie" Nordrhein-Wesfälische Akademie der Wissenschafter, Vortäge N444 (2000).

techmedica™ Brochure on Bone Modeling/Custom Prosthesis/Bone Staple System, Bulletin No. 1004, 10 pages (1982).

Biomet Orthopedics, Inc. Brochure "Patient-Matched Implants," 12 pages, Form No. Y-BMT-657/031500/M (Unknown Date).

DeSoto et al., "Three dimensional distortion in magnetic resonance images" Engineering in Medicine and Biology Society, 1989. Images of the Twenty-First Century., Proceedings of the Annual International Conference of the IEEE Engineering in, Issue Date: Nov. 9-12, 1989.

Minns, "Surgical instrument design for the accurate cutting of bone for implant fixation", Dryburn hosp., regional medical physics dep. Durham DH1 5TW United Kingdom Clinical materials, 1992, vol. 10, No. 4, p. 207-212.

Munting et al., "Effect of a stemless femoral implant for total hip arthroplasty on the bone mineral density of the proximal femur. A

(56) References Cited

OTHER PUBLICATIONS prospective longitudinal study", *J Arthroplasty*, 1997 12: Department of Orthopaedic Surgery, St-Luc University Hospital, Louvain University, Brussels, Belgium.

Munting et al., "Fixation and effect on bone strain pattern of a stemless hip prosthesis", *Journal of Biomechanics*, vol. 28, Issue 8, pp. 949-961, Aug. 1995.

Liu, et al., "Model-based 3D segmentation of the bones of joints in medical images" *Medical imaging 2005: Image Processing, Proc. of SPIE* vol. 5747 (SPIE, Bellingham, WA 2005) 1605-7422/05.

Patient Matched PMI Implants CAMRA 3-D Imaging Brochure, Biomet, Inc. (1990).

Nicholls, Trauma Grand Rounds, PMI (Patient-Matched Implants) Brochure, Biomet Orthopedics (Feb. 29, 2000).

Hutmacher, Scaffolds in tissue engineering, Biomaterials, 2000 Elsevier Science Ltd. (pp. 2529-2543).

Rhodes, et aL., "An Application of Computer Graphics and Networks to Anatomic Model and Prosthesis Manufacturing", MPDI Medical Science Center, Charles Woznick Techmedica, Inc., IEEE CG & A, pp. 12-25, (Feb. 1987).

Kunz, Manuela et al., "Computer-Assisted Hip Resurfacing Using Individualized Drill Templates", The Journal of Arthroplasty, vol. 25, No. 4, p. 600-606 (2010).

Bobic, "Treatment of Full Thickness Injuries in Articular Cartilage," International Society of Arthroscopy, Knee Surgery and Orthopaedic Sports Medicine (ISAKOS) Day 1—May 29, 1999, www.medscape.com.

\* cited by examiner

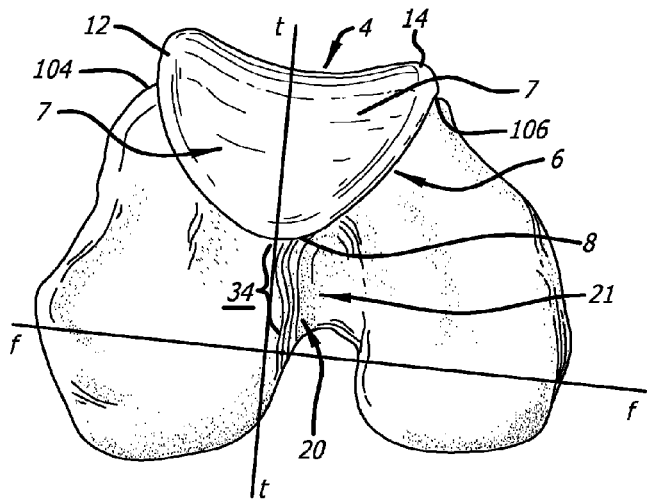
FIG. 3
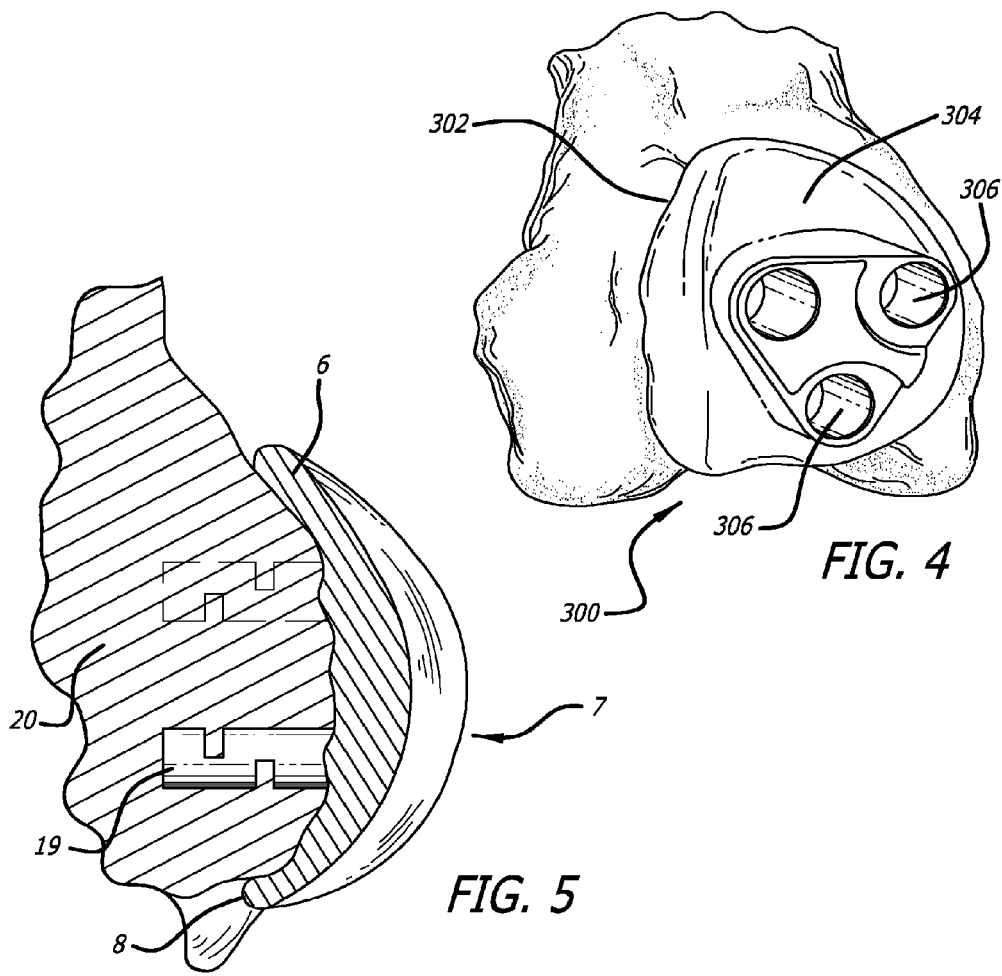
FIG. 4
FIG. 5

MARKING TEMPLATE FOR INSTALLING A CUSTOM REPLACEMENT DEVICE FOR RESURFACING A FEMUR AND ASSOCIATED INSTALLATION METHOD

RELATED APPLICATIONS

This application is a Continuation of U.S. utility application Ser. No. 13/096,868, filed Apr. 28, 2011, still pending, which is a Continuation of U.S. utility application Ser. No. 12/120,581, filed May 14, 2008, now issued as U.S. Pat. No. 7,935,150, which is a Continuation of U.S. utility application Ser. No. 11/030,868, filed Jan. 7, 2005, now issued as U.S. Pat. No. 7,517,365, which is a Divisional of U.S. utility application Ser. No. 10/712,436, filed Nov. 12, 2003, now issued as U.S. Pat. No. 6,905,514, which is a Divisional of U.S. utility application Ser. No. 09/528,128, filed Mar. 17, 2000, now issued as U.S. Pat. No. 6,712,856, the contents of all of which are herein incorporated by reference in their entirety.

BACKGROUND OF THE INVENTION

1. Field of Invention

The invention relates generally to a replacement device for a knee joint, and more particularly, to a device for resurfacing the trochlear groove of a femur that is customized to an individual and to methods for installing and making the same.

2. Description of the Related Art

The human knee joint primarily includes three parts, anatomically referred to as the femur (thighbone), the tibia (shinbone) and the patella (kneecap). The knee joint is then further subdivided into two joints: the patella-femoral joint (space between the kneecap and distal anterior surface of the thighbone) and the tibia-femoral (space between the thighbone and shinbone).

During normal bending and straightening of the leg, the patella (kneecap) slides over the femur (thighbone) within a groove that is located on the front distal surface of the femur. This groove is referred to as the trochlear groove. Several types of abnormalities can occur with the movement of the patella over the femur. For example, the patella may dislocate or slip out of place, it may fracture, or develop a tracking problem. Normally, the patella tracks, or glides within the central region of the trochlear groove. A tracking problem occurs when the patella no longer remains centered within the groove as it glides over the femur. The resulting abnormal biomechanics can cause chronic pain in the joint and if left untreated, it can lead to degenerative arthritis.

The distal end of the femur (within which resides the trochlear groove) is covered with articular cartilage. This cartilage functions as a cushion between the femur and the tibia. In arthritis of the knee joint, the articular cartilage breaks down, either from abnormal wear as mentioned above, or from injury, age, congenital predisposition, inflammatory arthritis, or obesity, etc. When this cartilage breaks down, the cushion is lost, resulting in pain, swelling, bone spur formation and/or decreased range of motion of the knee joint.

Due to the inability of damaged cartilage to repair itself after injury, the range of treatment for patients with unicompartmental disease involving the patella is limited. The most commonly prescribed treatments included soft tissue releases and/or realignment of the patellar tendon, patellectomy, where the patella is completely removed, or a total knee replacement with a standardized patello-femoral-tibial prosthesis. In certain instances none of these procedures may be desirable or effective. For example, the soft tissue procedures may not work. A patient having undergone a patellectomy is left partially crippled due to the loss of the kneecap, which served to hold the joint together. Additionally, these patients often still suffer from pain due to contact of the remaining tendon moving directly over the groove. A total knee replacement with a standardized prosthesis is also far from ideal because much of the femur bone must be carved away in order to "fit" the distal surface of the femur to the standardized prosthesis. Additionally, the patients are often young and are likely to require replacement of the prosthesis. Each revision operation is more difficult. Therefore, there still is a need for a better treatment of patients with degenerative arthritis of their patella-femoral joint.

The present invention provides a replacement device that is customized to each individual knee joint. Due to the "fitting" of the replacement device to the patient's femur, instead of the reverse as is the case with standard prosthetic devices, the patient's original range and force of motion (kinematics) through the knee joint is preserved and the patient does not suffer from device-related pain. Also included is a method for making a customized replacement device and a marking template for such a device. Bone stock removal is limited and functionally is maximized.

BRIEF SUMMARY OF THE INVENTION

The present invention is directed toward a custom replacement device for resurfacing an articulating or joint surface of the femur and methods of making and installing such a device. This custom replacement device overcomes the problems associated with prior knee joint replacement devices or prostheses in that it is made specifically to fit the trochlear groove surface (surface over which the patella slides) of a femur from an individual patient. Thereby creating a "customized" replacement device for that individual femur.

The replacement device is substantially defined by four outer points and first and second surface areas. The first of four points is defined approximately as being 3 to 5 mm from the point of attachment of the anterior cruciate ligament to the femur. The second point is defined approximately at or near the superior edge of the end of the natural cartilage. The third point is defined approximately at the top ridge of the right condyle. The fourth point is defined approximately at the top ridge of the left condyle. The first surface area is customized to substantially match the bone surface area of the trochlear groove of the femur. The second surface area has a tracking path that is approximately perpendicular to the end of the condyles of the femur. The thickness between the first and second surface areas may be approximately between 2 mm and 6 mm. To couple the replacement device to the femur, a pin protruding from the first surface area may be used to penetrate an opening in the femur prepared by a surgeon. Boney ingrowth may secure the prosthesis or bone cement may be used.

The replacement device can also include a customized drill guide that is substantially defined by first and second surface areas. The first surface area is customized to the surface area of the trochlear groove of the femur. The second surface area includes a hole that is aligned substantially to the pin to assist in drilling the opening into the femur for the pin.

In accordance with one aspect of the present invention, these and other objectives are accomplished by providing a replacement device having a top surface; a bottom surface; the bottom surface substantially formed to match the trochlear groove surface of a femur; and the top surface substantially tracking the trochlear groove of the femur.

In accordance with another aspect of the present invention, these objectives are accomplished by providing a system for installing a replacement device to a distal end of a femur having a trochlear groove surface, comprising: a marking template, wherein: the marking template has a back side substantially matching the distal end of a femur; and an opening through the marking template; a drilling apparatus to form a hole on the distal end of the femur assisted by the opening in the marking template; and a replacement device, wherein: the replacement device has a bottom side substantially matching the distal end of the femur; and a pin protruding from the bottom side of the replacement device adapted to insert into the hole on the distal end of the femur.

In accordance with yet another aspect of the present invention, these objectives are accomplished by providing a method of making a replacement device, comprising the steps of: forming a model of a distal end of a patient's femur; forming a first mold from the model, wherein the first mold has a bottom side that substantially matches the trochlear groove of the patient's femur, wherein the first mold has a top side opposite of the bottom side; coupling a peg on a predetermined location on the bottom side of the first mold; shaping the top side of the mold to substantially track the trochlear groove of the patient's femur; forming a second mold from the first mold; and pouring viscous material into the second mold to make a replacement device.

In accordance with still another aspect of the present invention, these objectives are accomplished by providing a replacement device having a bottom side that substantially matches the trochlear groove of a patient's femur, wherein the bottom side of the replacement device has a pin at a predetermined location; providing a marking template having a back side that substantially matches the trochlear groove of the patient's femur, wherein the marking template has an opening corresponding to the predetermined location of the pin; removing the cartilage from the distal end of the femur; positioning the marking template about the femur substantially similar to the desired installed position of the replacement device; drilling a hole on the distal end of the femur though the opening of the marking template; removing the marking template from the femur; and inserting the pin of the replacement device into the hole of the femur to install the replacement device on the desired location of the femur.

Alternatively, a method of forming a customized replacement device for a femur will include the steps of duplicating the surface of the distal anterior femur from an individual; and using the duplicate to form a back surface of the customized replacement device and/or a customized marking template.

BRIEF DESCRIPTION OF THE DRAWINGS

FIG. 3 is an another perspective view of the femur with the replacement device coupled to the femur;

FIG. 4 is yet another perspective view of the femur associating with a custom marking template having guide holes that correspond to the pin on a replacement device, residing on the trochlear groove surface of the femur;

FIG. 5 is a cross-sectional view of the replacement device residing on the femur, along the line 5-5 in FIG. 2;

DETAILED DESCRIPTION OF THE INVENTION

This description is not to be taken in a limiting sense, but is made merely for the purpose of illustrating the general principles of the invention. The section titles and overall organization of the present detailed description are for the purpose of convenience only and are not intended to limit the present invention.

One of the features of the present invention is to provide a replacement device for a patient's knee joint that replicates as closely as possible the original kinematics of the patient's knee. More particularly, the replacement device substantially replicates patient's actual trochlear tracking pattern of the femur to maintain the original articulating movement of the knee. To do so, unhealthy articular cartilage is removed and replaced with the replacement device, which is custom fitted for a patient's femur to maintain as closely as possible the original articulating movement of the patella about the trochlear groove. That is, the replacement device is custom fitted so that the underside of the patella articulates about the femur approximately two (2) to six (6) mm away, which mimics what a patella on a healthy articular cartilage would articulate from. The above feature may be accomplished by providing a trochlear groove that is formed along the replacement device that tracts the trochlear groove on the femur. Moreover, as further discussed below, the underside of the replacement device substantially matches the face of the femur, to minimize any error in positioning the replacement device about the femur. With this introductory in mind, more detailed description of the invention is discussed below.

Figure 2:
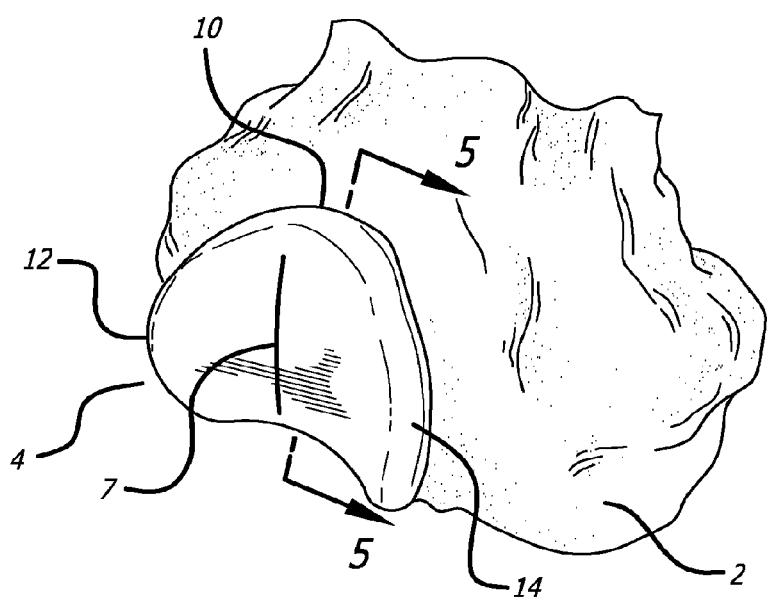
FIG. 2 is a perspective view of an embodiment of the present invention illustrating an exemplary replacement device coupled to the distal end of a femur.
Figure 9:
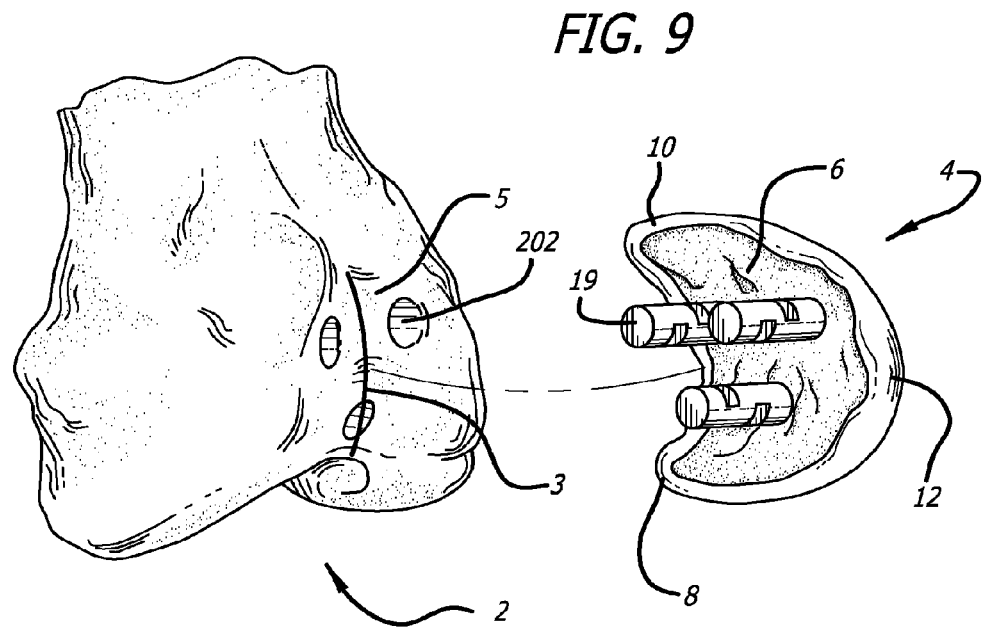
FIG. 9 is a perspective view showing a patellar face side of a human femur and a back side view of a replacement device prior to placement of the replacement device onto the femur.
Figures 7, 8:
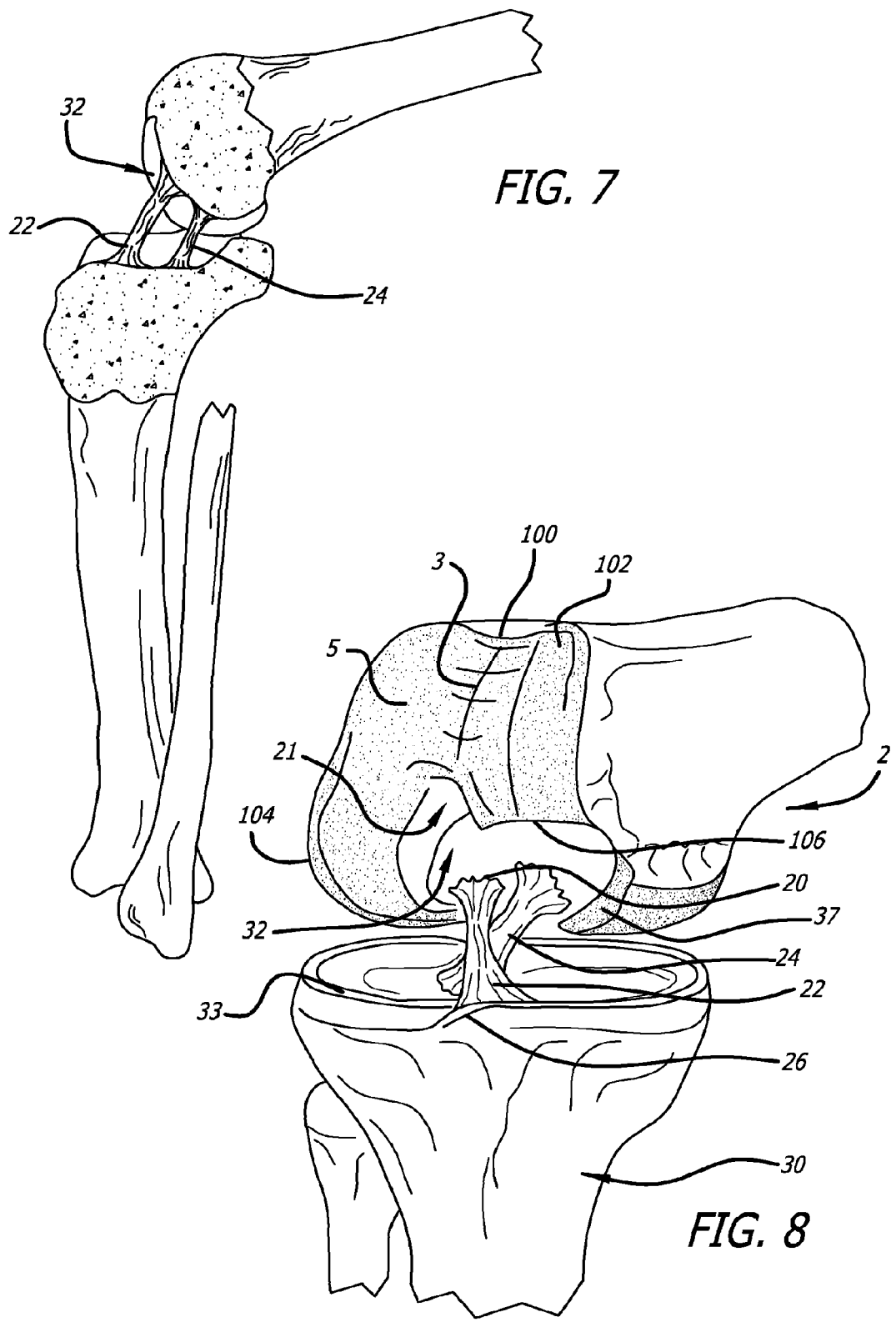
FIG. 7 is an exemplary illustration of a human femur attached to a tibia by the anterior and the posterior cruciate ligaments.
FIG. 8 is an expanded view of a human knee joint in a bent position.

As illustrated by way of example in FIGS. 2 and 9, one embodiment of the present invention includes a custom replacement device 4 adapted to associate with the distal end of a patient's femur 2. FIG. 2 shows a model made of the patient's femur in FIG. 9. The model 200 is substantially similar to the patient's femur 2 and is used to make the custom replacement device 4 (as discussed below). The surface near the distal end of the femur 2 defines a patellar face 5, and along the patellar face is a trochlear groove 3 of the femur. FIGS. 7 and 8 show exemplary views of a normal, intact knee joint. Referring to FIG. 8, on a healthy knee, the trochlear groove would be covered with about 5 mm of articular cartilage 100. However, if the articular cartilage wears down for any reason, the cushion and sliding surface that the cartilage provides is lost, resulting in pain, and therefore may need to be replaced with the custom replacement device 4.

Figure 1:
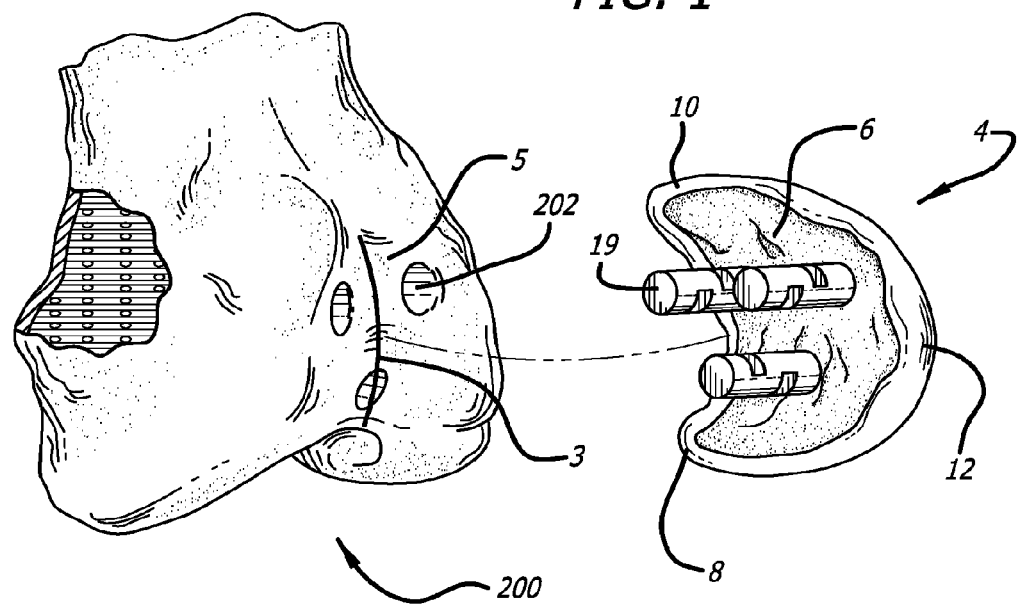
FIG. 1 is a perspective view of a femur showing the patellar side with its trochlear model groove, and the replacement device adapted to couple to the femur.

One of the advantages with the replacement device 4 is that it is custom fitted for a patient's femur so that the replacement device 4 replacing the articular cartilage will maintain as closely as possible the original kinematics of the patient's knee. That is, the replacement device 4 is customized specifically to fit the patellar face 5 surface and trochlear groove 3 region of the femur 2. In this regard, as illustrated in FIGS. 1 and 9, the back surface 6 of the replacement device 4 substantially matches the surface area of the patellar face 5 of the femur 2. Moreover, the back (bottom) surface 6 also matches and fits to the contours of the trochlear groove region 3 of the patellar surface 5. The custom replacement device is coupled to the femur through one or more hole(s) 202 in the distal end of a human femur. The hole(s) 202 can be made by a surgeon and may be located so as to reside along the trochlear groove region 3 of the human femur 2. As shown in FIG. 5, the replacement device can be implanted into the femur via a pin 19 inserted into the one or more corresponding hole 202, thus resurfacing the patellar face surface of the human femur. The front (top) surface 7 of the replacement device is contoured to maintain the tracking of the patella centrally within the front surface during articulation of the patella about the trochlear groove (FIG. 2).

As illustrated by way of example in FIGS. 1 and 2, the replacement device 4 may be substantially defined by four boundary conditions 8, 10, 12, 14, along with the back surface 6 and the front surface 7. By way of background, a human knee joint includes two cruciate ligaments which are located in the center of the knee joint. As shown in FIG. 8, these two ligaments, referred to in the art as the anterior cruciate ligament (ACL) 22 and the posterior cruciate ligament (PCL) 24, are the primary stabilizing ligaments of the knee. The ACL 22 attaches, at its bottom 26, to the tibia 30, and, passes obliquely upward to insert 20 into the inner and back part 32 of the outer condyle 15 of the femur 2. Attachment of the ACL to the femur stabilizes the knee joint along the rotational axis and prevents the femur from sliding backwards on the tibia (or the tibia from sliding forward on the femur).

In one embodiment of the present invention, the distal portion of the patellar tongue or first boundary condition of the replacement device may be designed to not extend far back to impinge upon the tibial surface or cartilage of the tibia. Therefore, the first boundary condition of a replacement device may be defined to be approximately 3 to 5 mm from the point of attachment of the ACL to the patient's femur. Specifically, as illustrated in FIGS. 3 and 8, the first boundary condition 8 may be approximately 3 to 5 mm from the point of attachment 20 of the anterior cruciate ligament 22 to the femur 2. In other words, there is approximately 3 to 5 mm distance between the patellar tongue region (first boundary condition) 8 and the attachment 20 of the anterior cruciate ligament 22. Alternatively, the first boundary condition of a replacement device 8 is of a sufficient distance above the groove 21 where the ACL exits so as not to result in impingement upon the tibial surface 33 during functioning.

Referring to FIGS. 1 and 8, the second boundary condition 10 may be defined approximately at or near the superior edge 100 of the end of the natural cartilage 102. As shown in FIGS. 3 and 8, the third boundary condition 12 may be approximately at the top ridge of the right condyle 104. The fourth boundary condition 14 may be approximately at the top ridge of the left condyle 106. The four boundary conditions 8, 10, 12, 14 and front 6 and back 7 surface, as described above, may substantially define the perimeter or outer edges of the replacement device in approximately an oval shape. However, the replacement device need not be defined by any one of the four boundary conditions. Alternatively, the replacement device may be defined by any one of or any combination of the four boundary conditions. Of course, the perimeter or outer edges of individual replacement devices may differ depending on the unique anatomic characteristics of an individual patient's femur. Besides the four boundary conditions, the back surface 6 is customized to match the patellar face 5 of the femur 2 (FIG. 1). Moreover, edges of the replacement device may be streamlined to have smooth or rounded edges so that the replacement device may come in direct contact with the bony surface of the femur without etching away at the femur. Still further, the streamlined edges prevents tearing or damaging the soft tissue around the knee.

As further illustrated in FIGS. 2 and 3, the front surface 7 is generally concave, which is formed by the inner and outer lateral (side) lip regions being raised to contour around the third and fourth boundary conditions 12 and 14, respectively. Accordingly, as illustrated by way of example in FIG. 3, the longitudinal path of the resulting front surface substantially replicates the actual trochlear groove-tracking pattern for a healthy knee generally in two ways. The first way is to create a mold that substantially replicates the distal end of a patient's femur (as discussed below); and based on the geometry of the replicated mold, the patient's trochlear groove tracking pattern can be determined off of the mold. As illustrated by way of example in FIG. 3, the second way is to align the tracking pattern (axis t-t) along the front surface area 7 so that it is approximately perpendicular to the ends of the condyles 104 & 106 of the femur 2, i.e., and aligned with the center of the femoral head (axis f-f); as most patients have a tracking pattern that is generally perpendicular to the ends of the condyles. Thus, the first method can be used to check the alignment of tracking pattern calculated by the second method, and vice versa. Alternatively, the tracking pattern produced by both methods can be combined to produce an average tracking pattern of both methods. Either way, the tracking pattern produced by both methods will substantially replicate the correct trochlear groove-tracking pattern. Without such customization of the replacement device, there are too many variations amongst patients' knees such that the original kinematics for a patient could not be reproduced. In addition, standard devices require the removal of large amounts of bone in order to make them fit onto the femur. Still further, other known or new methods of tracking the patient's trochlear groove of the femur may be used.

Figure 6:
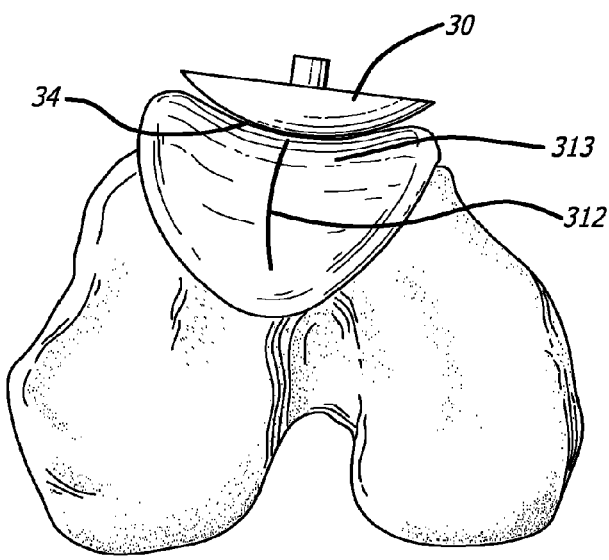
FIG. 6 is the perspective view of FIG. 4 with a patella residing on the trochlear groove surface of the replacement device.

As illustrated by way of example in FIG. 6, the tracking pattern is generally formed along the base of concave surface 313 of the replacement device 4, thereby maintaining the patella 30 centrally within the device 312. Therefore, regardless of the direction or angle of movement of the patella and tibia (shin bone) along the replacement device, the trajectory of the patella will be maintained centrally within the intercondyle space and the patella will glide smoothly within the central line due to the increased curvature of the device along its lateral and medial or side lip regions. This allows the present invention to use a standard dome patellar prosthesis 30 such as the Kinamed, Inc. GEM Knee System patella, which has a large contact area 34 with the device, to distribute the stress applied to the patella and the device. So that even if there is a slight misalignment with replicating the trochlear groove of the femur, if at all, there is room for error and still full contact across the surface of the patella to distribute the load in an optimal manner. Accordingly, the patella will repeatedly glide over the front surface of the replacement device, reliably, and there is little chance, if at all, that the patella will dislocate from the tracking surface of the replacement device. In addition, the large contact area distributes the load and minimizes peak contact stress in the polyethylene thus reducing wear debris generation.

In the past, replacement of a diseased knee joint required surgical modification of the surface of the femur so as to allow a close "fit" of the prosthetic device within the new joint. This required extensive removal or carving of the cartilage and bone surfaces of the head of the femur in order to "match" with the back surface of a standardized prosthetic device.

With the present invention, there is almost no removal of original bone and therefore, no loss of requisite anatomical structures. Insertion of the replacement device requires minimal removal of existing anatomic structures, if at all. Therefore, the intent is to remove only the diseased portion (the natural cartilage) of the patient's knee joint prior to installing the replacement device.

In a healthy knee joint, the average thickness of the articular cartilage 102 at the knee joint is about 4 to 5 min (FIG. 8). In other words, there is about 4 to 5 mm of articular cartilage covering the femur, so that the patella articulates about 4 to 5 mm from the trochlear grove of the femur. In the case of unhealthy cartilage, where the replacement device is needed, the unhealthy cartilage is removed and replaced with the replacement device, which has been custom made for the patient's femur. To replicate as closely as possible the original kinematics of the patient's patello-femoral joint, as illustrated by way of example in FIG. 2 (and further detailed in FIG. 5), the thickness between the back 6 and front 7 surface areas of the replacement device may vary approximately between 2 mm and 6 mm. In other words, the thickness of the custom replacement device may be approximately that of the patient's original articular cartilage. To further enhance the interaction between the custom replacement device 4 and the femur 2, a pin 19 may be located at a predetermined position along the back surface 6 of the replacement device. One or more pin(s) 19 can protrude from the back surface area to enhance the association of the replacement device with the femur. As illustrated in FIG. 9, the replacement device may have three pins that insert into the corresponding holes in the femur, so that there will be very little play, if any, once the pins are inserted into the holes. Alternatively, other apparatus and methods may be used to couple the replacement device to the femur, for example, a bone ingrowth surface or adhesives, including cement, may be applied between the replacement device and the femur. Still another alternative may be a screw or bolt, where the screw penetrates through the opening in the replacement device and into the femur. In other words, any known or new apparatus or methods may be used to couple the replacement device to the femur.

By way of background, a bone ingrowth surface is a surface treatment applied to an implant which is designed to allow the patient's bone to attach or ingrow into the prosthesis, and thereby securing the prosthesis to the bone. The surface coating can assume a number of different forms. For example, commonly used is a process where a layer is physically attached to the prosthesis through titanium plasma spraying. Other techniques involve sintering small beads or mesh to the surface or applying a layer of hydroxyapatite may also be used.

With regard to surgically implanting the replacement device, as illustrated in FIG. 4, a customized marking template 300 may be provided that is substantially defined by first (back or bottom) and second (front or top) surface areas 302 and 304, respectively. Like the back surface 6 of the replacement device 4, the first surface area 302 of the marking template 300 is customized to match the surface area of the trochlear groove 5 of the femur so that the marking template will be positioned properly with the femur. The second surface area 304 includes a hole 306 or holes (depending upon the number of pins protruding from the replacement device) that is in a predetermined position to align substantially to the pin on the customized replacement device. Furthermore, the holes or slots 306 of the second surface area 304 of the custom marking template, extend through to the first surface 302 of the custom marking template. Therefore, each hole or holes 306 in the predetermined positions of the marking template serve as guides for formation of openings 202 in the femur 2 of the patient into which the pin(s) 19 will be inserted. Moreover, the custom marking template 300 may be substantially defined by four boundary conditions as in the replacement device 4. Accordingly, the custom marking template 300 as shown in FIG. 4, assists the surgeon in identifying the perimeter of the custom replacement device 4 as well as the location of opening 202 (depending upon the number of pins protruding from the back surface area 6 of the custom replacement device 4) that will be drilled into the patellar face surface of the femur 2.

To surgically implant the replacement device to the patellar face 5 of the femur 2, a surgeon may first need to remove some or all remaining diseased or damaged articular cartilage 102 on the patellar surface 5 of the femur (FIG. 8). The surgeon may then scrape away the articulate cartilage until a substantial bony surface 37 of the patellar face shows. FIG. 8 shows a view of a patient's femur prior to preparation by the surgeon for insertion of a replacement device. Thereafter, the marking template 300 is aligned and positioned onto the patellar face to drill the necessary openings for the pins (FIG. 4). Since the first surface area 302 of the marking template matches the contours of the patellar face 5 along with the four the boundary condition 8, 10, 12 and 14, the surgeon is assured that the marking template is aligned and positioned properly. In other words, the custom marking template can be used to guide the surgeon in marking the location of the openings and thereby aid in the formation of the openings at their appropriate location or predetermined positions. Once the marking template is in position, the surgeon can precisely drill the openings, aided by the holes or slots on the marking template, using any drilling method known to one of ordinary skill in the art. FIG. 9 shows a representative femur 2 where the diseased natural cartilage has been removed, thus exposing the bony surface of the patellar face 5 of the femur and the openings 202 into which the pin(s) 19 of the replacement device 4 will insert.

With the necessary openings 202 precisely drilled into the patellar face 5 of the femur, the marking template is removed and replaced with the replacement device 4. As illustrated in FIG. 9, the custom replacement device is placed onto the femur by insertion of the pin 19 or pins protruding from the back surface of the custom replacement device, into the corresponding openings in the predetermined location formed in the patellar face surface of the femur. The custom replacement device can be affixed to the bone 20 by a surgical cement, such as Howmedica Simplex P Cement, or any other method known to one ordinarily skilled in the art. Once in place, the replacement device provides the patient substantially full motion originally provided by the native anatomical knee joint. In other words, in most, if not all, positions of the leg, and throughout the normal range of movement of the leg, the custom replacement device permits normal rotation and lateral movement substantially similar to the original kinematics of the healthy knee joint. Therefore, the replacement device 4 gives the patient the "most natural" replacement of the knee possible. Note that with the present invention, there is no need to carve away at the femur, since the backside of the replacement device matches the surface of the femur.

Figure 10:
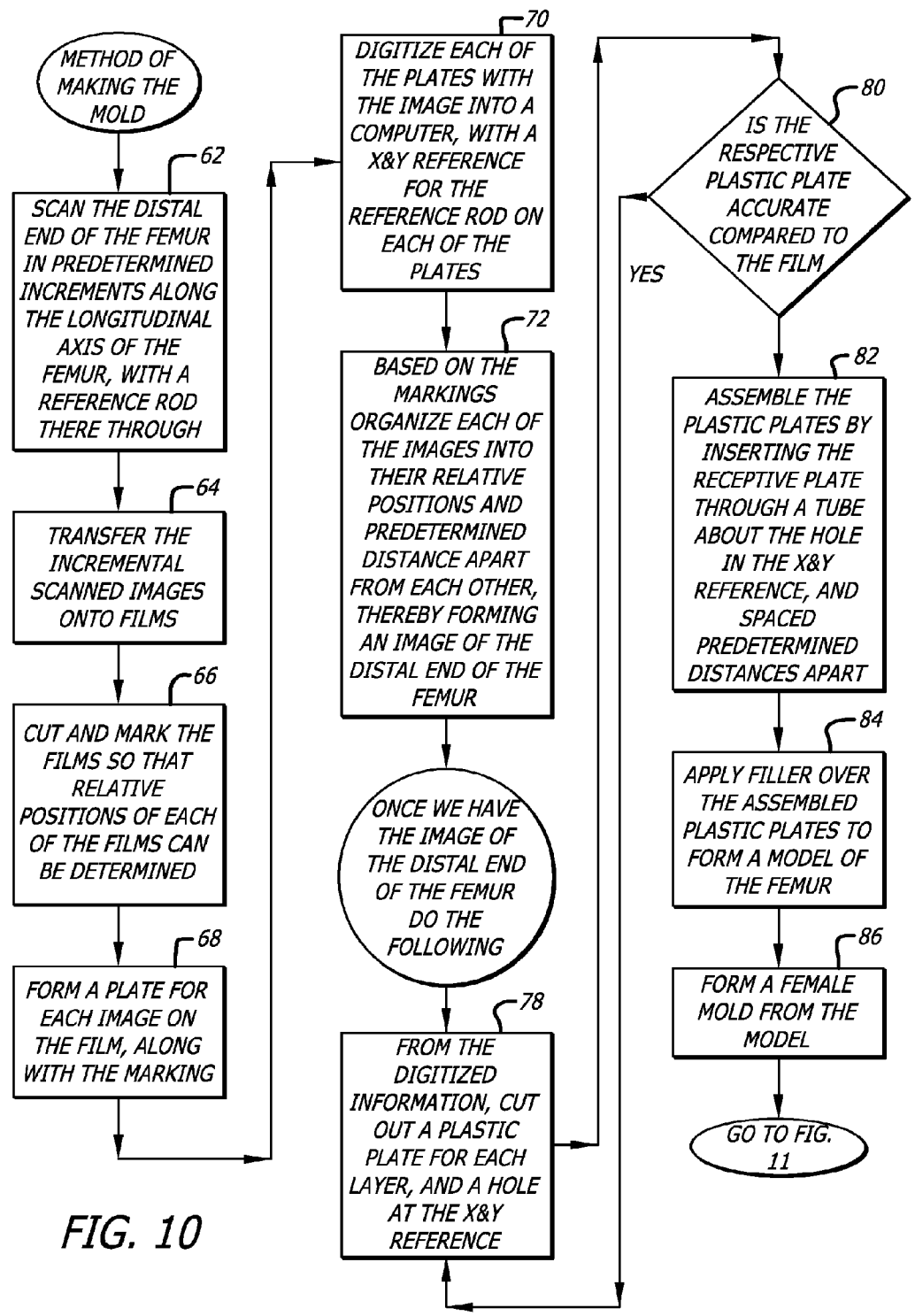
FIG. 10 is a diagrammatic chart of a method of making a mold for constructing a replacement device.
Figure 11:
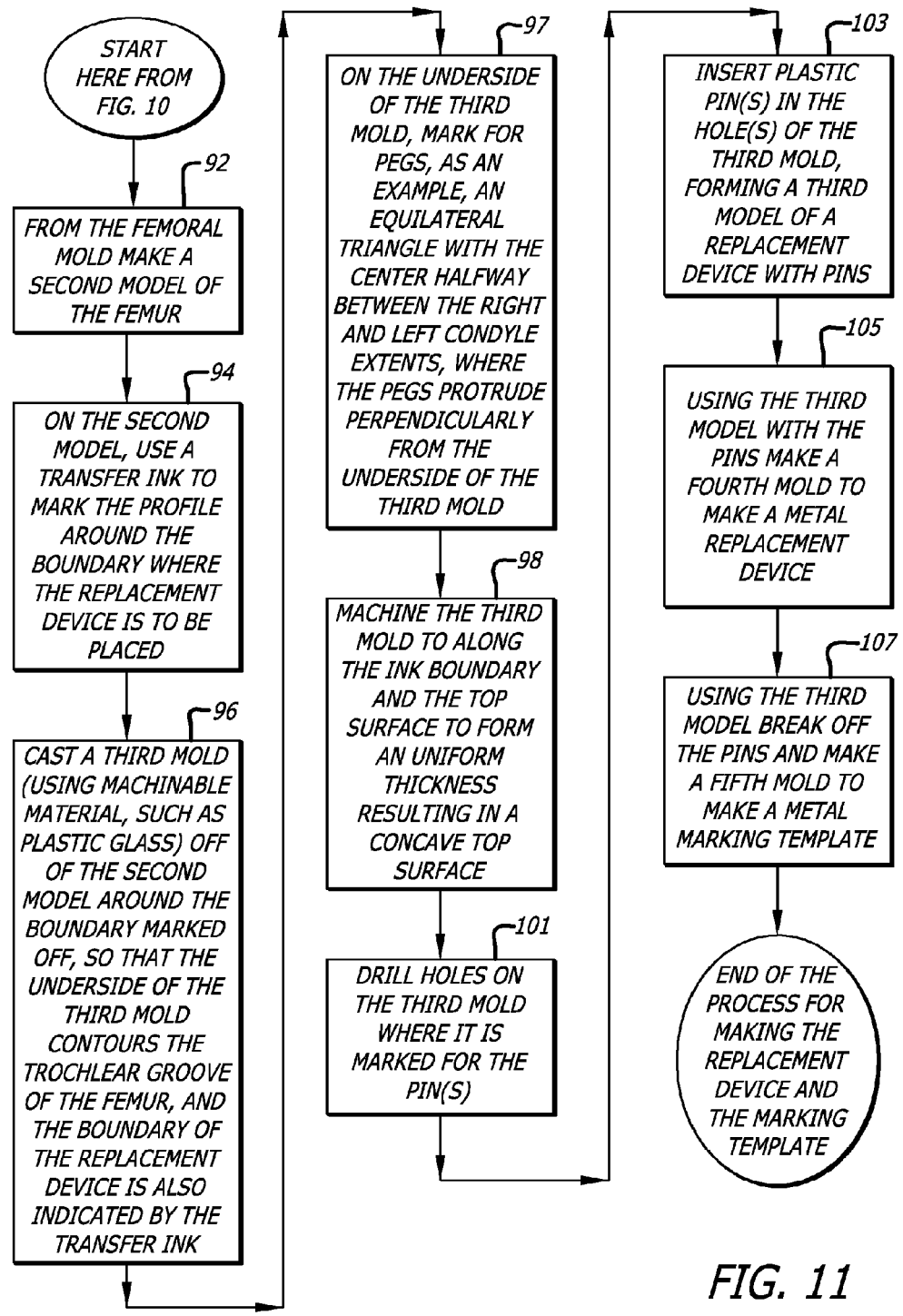
FIG. 11 is a diagrammatic chart of a method of making a replacement device and a marking template from a femoral mold.

FIGS. 10-11, illustrate by way of example an exemplary method of producing the replacement device 4 and the marking template. Initially, a three-dimensional model of the distal end of the femur is formed. This may be accomplished in step 62, where the distal end of the femur is CT scanned to form a number of slices that are predetermined distances apart along the longitudinal axis of the femur, such that when the slices are assembled they form a three-dimensional contour of the femur. Furthermore, to ensure that the slices are aligned properly when they are assembled, a reference point, such as X and Y coordinate may be marked on each of the slices as a reference point. For example, the scanning may be done through a X-ray or CT scan protocol that defines a number of slices to be taken, and the starting and stopping marks to determine where to start and stop scanning. Moreover, in critical areas as in the trochlear groove of the femur where accuracy is particularly important, the distance between the slices may be reduced to more accurately define the contour of the femur in that area. In this regard, the slices may generally be about 3 mm apart, but for more accuracy the slices may be about 1.5 mm apart. Of course, the distance between the slices may further vary depending on the accuracy desired. In other words, in such areas where more detail regarding contour is desired, like the four boundary regions 8, 10, 12 and 14, and the trochlear groove 5 region, the distance between the slices may be reduced to about 1.5 mm or less.

To further improve the accuracy of the sliced images of the femur, an X-ray motion detection rod may also be used to detect movement by the patient while the CT scan is taken. That is, while the CT scan is taken, any movement by the patient can distort the accuracy of sliced images. To correct for this distortion, a detection rod may be used to detect the movement of the patient, by moving with the patient, so that when the sliced images are later analyzed, the movement by the patient can be detected and the sliced images can be adjusted for the movement. Still further, a scaling rod may also be used to ensure that the sliced images are at a proper scale so that when the sliced images are assembled, the size of the femur model is correct.

As illustrated in step 64, once the sliced images are taken of the femur, each sliced image is transferred onto a film, and reviewed for a number of features, such as clarity, scaling, and whether the images were taken according to the protocol. If the images were properly taken, then in step 66, each of the film is cut around the perimeter of the sliced image of the femur. Each cut film may also be marked so that relative position of each of the cut film can later be determined In step 68, from all of the cut films, a respective small plate may be made from each of the cut films having the image of the cut film and the marked information: In step 70, these plates are then used to digitize the image into a computer.

In step 72, with digitized information of each individual slices, and the spacing between the sliced images, a computer aided design (CAD) system with a macro may be used to lay all of the sliced images on to a planar format. In the planar format, knowing the relative position of each sliced images relative to one another, reference holes are drawn to each of the images, so that when the slices are assembled about the reference holes, an accurate model of the femur may be reproduced. The digitized sliced images are assembled about the reference holes to view the computer generated image of the femur.

In step 78, to replicate a femur from the digitized information, a Computer Aided Manufacturing (CAM) file may be used to cut plastic plates of the digitized information. For example, a laser or any other method known to one of ordinary skill in the art may be used to cut the plastic plates representing the perimeter of the sliced images of the femur, along with the reference holes. Accordingly, individual plastic plates representing a respective sliced image of the femur is produced. In step 80, these plates may be checked for accuracy and quality against the films produced earlier. Of course, if the cut plate does not correspond with the respective film then another plate may be cut to match the image and scale of the film.

In step 82, with the accurate plates, they are assembled in their respective positions and spaced apart according to the distance in which the sliced images were taken. That is, plates are orderly inserted into a rod through the reference holes so that the plates align properly. Furthermore, as stated above, in areas where accuracy is important, the slices may be about 1.5 mm apart, while other slices may be about 3 mm apart. The distance between the plates is maintained by a spacer between the plates, where the thickness of the spacer will also vary depending upon the desired accuracy. The thickness of the plates, themselves, may also vary depending on the desired accuracy. In other words, in the trochlear groove area the plates themselves may be thinner and spaced closer together to other plates. With regard to the spacers, they may be formed from the reference hole pieces cut from the plates.

In step 84, with the plates assembled, using the edges of the plates as the outer boundary, the spaces between the plates and the incremental differences in the outer boundary of the plates are covered with filler, such as clay, to form an outer surface of the femur (also shown in FIG. 1). In other words, just enough filler is used to cover the edges of the plates to smooth out the edges between the plates to define the outer face of the femur. This forms a model of the distal end of the femur. Although one method of forming a model is discussed here, other known or new methods of forming a model of the femur may also be used. For example, the CT image data may be compiled in a computer, a surface created, and the model machined directly using the surface data to drive a computer assisted machining system.

In step 86, from the model, a mold is made. This can be done for example by placing the model into a standardized box and pouring liquid rubber into it to make a mold. Referring to FIG. 11, in step 92, with the mold, a second model of the femur may be made by pouring, such liquid as urethane into the mold. This step may be repeated to make three models of the femur. Two of the models may be sent to the physician to review and check for accuracy and affirm the exact location of the boundary points.

In step 94, with the second model of the femur, the boundaries are marked where the replacement device is to be placed on the femur. Then the edges of the second model are squared off such that it is outside the marked boundaries where the replacement device is to be located. Additionally, the four boundary conditions that may substantially define the replacement device, along with the outer perimeter of the device may be marked using transfer ink on the second model. Thereafter, in step 96, a third mold may be made using machinable material such as plastic glass, from the squared off second model so that the underside of the third mold contours the trochlear groove of the femur and marked with the transfer ink indicating the perimeter of the replacement device. In step 97, on the underside of this third mold is marked for pegs.

The third mold is then machined or sanded along the top surface to generally give it a uniform surface throughout. For example, the top surface of the third mold may be sanded until a uniform thickness of 5 mm is relatively formed or to a desired thickness between the top and bottom surfaces of the replacement device. Additionally, the edges of the third mold are also machined to give it desired finish. Accordingly, a mold for the replacement device may be made of plastic glass, for example, generally having an oval shaped defined by the four boundary conditions and the concave upper surface. To improve the accuracy of the mold, the third mold may be made slightly larger than the actual size of the replacement device, as cast mold has tendency to shrink. As an example, the mold may be made about 2% larger than the actual size of the replacement In step 101, to form a pin that protrudes from the underside of the replacement device, a hole for each of the pin is drilled through the third mold, and inserted with a peg representing the pin. As an example, underside of the replacement device may have three pins placed in equilateral triangle format to distribute the load evenly. Furthermore, the pins may be distributed in predetermined distance apart to standardize the drill pattern for all of the replacement device. Additionally, the equilateral triangular pins may have its center point about halfway between the right and left condyle extents, where the pins generally protrude perpendicularly from the underside of the replacement device.

In step 103, the metal replacement device and the marking template are made from the third mold having the pegs protruding from it. In step 105, to produce a replacement device, a fourth female mold is made from the third mold, using such material as rubber. From the female mold, liquid metal can be poured into it, to produce a metal replacement device. In step 107, to produce a marking template, the pegs on the third mold is removed and a fifth female mold is made, using such material as rubber. Then from the fifth female mold without the pegs, liquid metal is poured into it, to produce the marking template. Alternatively, any other method known to one of ordinarily skilled in the art of producing the replacement device and the marking template from the third mold is within the scope of the present invention. It is also possible to machine the replacement device directly by creating a computer model of the device and using said model to drive a machine tool to cut the model directly from a piece of material.

With regard to material, the replacement device 4 is made of a substantially firm, non-bioreactive material. Examples of such material include, surgical grade Co Cr alloy or other substantially rigid, bio-compatible material such as titanium, stainless steel, zirconia, or alumina ceramic. All surfaces of the device, which are external to the femoral bone (once the device is implanted), are highly polished and smoothed.

In closing, it is noted that specific illustrative embodiments of the invention have been disclosed hereinabove. Accordingly, the invention is not limited to the precise embodiments described in detail hereinabove. With respect to the claims, it is applicant's intention that the claims not be interpreted in accordance with the sixth paragraph of 35 U.S.C. .sctn. 112 unless the term "means" is used followed by a functional statement.

We claim:

1. An instrument comprising:
   a body, the body including a femoral contacting side, the femoral contacting side having a three-dimensional shape substantially custom formed to match and fit at least a portion of a distal-anterior portion of a femur of a particular patient; and
   a surgical tool guide, the surgical tool guide being customized for the particular patient wherein the surgical tool guide is in a pre-defined spatial arrangement with the three dimensional shape of the femoral contacting side and the particular patient.

2. The instrument of claim 1, wherein the femoral contacting side is pre-operatively configured to continuously match in shape a region of a femoral trochlea spanning from a medial side of the femoral trochlea to a lateral side of the femoral trochlea.

3. The instrument of claim 1, wherein the surgical tool guide comprises at least two drill guides configured to guide the formation of pin receiving openings in a distal portion of the femur of the particular patient.

4. The instrument of claim 1, wherein the femoral contacting side is a contiguous surface and is configured to contiguously match in shape to a femoral trochlea of the particular patient.

5. The instrument of claim 1, wherein the body defines an outer boundary surface configured to indicate an outer boundary of a femoral implant relative to the femur of the particular patient.

6. The instrument of claim 1, wherein the femoral contacting side is configured to match the particular patient's femoral trochlea surface to establish a pre-defined spatial arrangement of the instrument relative to an axis of the particular patient.

7. The instrument of claim 1, wherein the femoral contacting side has a shape that is configured to match a subchondral bone surface of the femoral trochlea of the particular patient.

8. The instrument of claim 1, wherein the femoral contacting side is generally concavely shaped in an anterior-posterior dimension and generally convexly shaped in a medial-lateral dimension.

9. An instrument for use during an implant procedure and customized for a particular patient, the instrument comprising:
   a body, the body including an articular region contacting surface, the articular region contacting surface having a three-dimensional shape substantially custom formed to match and fit at least a portion of a subchondral bone surface in a distal-anterior portion of a femur of the particular patient; and
   a surgical tool guide, the surgical tool guide being customized for the particular patient wherein the surgical tool guide is in a pre-defined spatial arrangement with the three dimensional shape of the articular region contacting surface and the particular patient.

10. The instrument of claim 9, wherein the articular region contacting surface is configured to match in shape at least a bottom portion of a trochlear groove of the particular patient.

11. The instrument of claim 10, wherein the articular region contacting surface is further configured to match in shape an anterior portion of the femur of the particular patient.

12. The instrument of claim 10, wherein the articular region contacting surface is configured to match in shape at least a portion of a trochlea of the distal femur of the particular patient, the portion spanning the trochlea from a medial side to a lateral side of the trochlea.

13. The instrument of claim 9, wherein the articular region contacting surface is configured to match in shape at least a portion of an area of an anterior-distal femur of the particular patient between two condyles of the distal femur.

14. The instrument of claim 9, wherein the articular region contacting surface is configured to match in shape at least a portion of an area of an anterior-distal femur of the particular patient between a superior edge of a cartilage surface and a point of attachment of an anterior cruciate ligament.

15. An instrument for use during an implant procedure and customized for a particular patient, the instrument comprising:
   a body, the body including an articular region contacting surface, the articular region contacting surface having a three-dimensional shape substantially custom formed to match and fit at least a portion of a cartilage surface in a distal-anterior portion of a femur of the particular patient; and a surgical tool guide, the surgical tool guide being customized for the particular patient wherein the surgical tool guide is in a pre-defined spatial arrangement with the three dimensional shape of the articular region contacting surface and the particular patient.

16. The instrument of claim 15, wherein the articular region contacting surface is configured to match in shape at least a portion of a distal-anterior portion of the particular patient's femur in an area inferior to a distal-anterior superior edge of the cartilage surface of the particular patient.

17. The instrument of claim 15, wherein the articular region contacting surface is configured to match in shape at least a portion of a distal-anterior portion of the particular patient's femur in a defined spatial arrangement relative to an axis of the femur of the particular patient.

18. The instrument of claim 15, wherein the articular region contacting surface is configured to match in shape to a trochlear groove of the particular patient's femur in a defined spatial arrangement relative to an axis of the femur that extends through a center of a femoral head of the particular patient.

19. An instrument for use during an implant procedure and customized for a particular patient, the instrument comprising: a body and a surgical tool guide, the body comprising a femoral contacting side, the femoral contacting side substantially custom formed to match in shape and size at least a portion of a distal-anterior portion of a femur of the particular patient and the surgical tool guide is in a pre-defined spatial arrangement with the three dimensional shape of the femoral contacting side and the particular patient.

20. The instrument of claim 19, wherein the femoral contacting side is a surface that is configured to match in shape at least a portion of a subchondral bone surface of the distal-anterior portion of the particular patient's femur.

21. The instrument of claim 19, wherein the femoral contacting side includes a surface configured to fit into a trochlear groove of the particular patient's femur.

22. The instrument of claim 21, wherein the surface configured to fit into the trochlear groove is configured to match in shape the trochlear groove of the particular patient's femur.

23. The instrument of claim 19, wherein the femoral contacting side is configured to match in shape the distal-anterior portion of the particular patient in a defined spatial arrangement relative to cartilage of the particular patient's distal femur.

24. The instrument of claim 19, wherein the surgical tool guide comprises a hole or a slot extending through the body of the instrument.

25. The instrument of claim 19, wherein the surgical tool guide comprises a plurality of holes extending through the body of the instrument.

26. The instrument of claim 19, wherein the surgical tool guide comprises at least one hole extending through the body of the instrument, the at least one hole configured to guide a drill for drilling an opening in the femur of the particular patient.

27. The instrument of claim 19, wherein the surgical tool guide comprises at least one hole extending through the body of the instrument, the at least one hole configured to facilitate positioning at least one pin in the femur of the particular patient.

28. The instrument of claim 19, wherein the instrument comprises a marking template.

* * * * *